United States Patent [19]
Ottosson et al.

[11] Patent Number: 6,047,600
[45] Date of Patent: Apr. 11, 2000

[54] METHOD FOR EVALUATING PIEZOELECTRIC MATERIALS

[75] Inventors: Mats G. Ottosson, Sunnyvale; Karen Hong, Mountain View, both of Calif.

[73] Assignee: Topaz Technologies, Inc., Sunnyvale, Calif.

[21] Appl. No.: 09/143,126

[22] Filed: Aug. 28, 1998

[51] Int. Cl.[7] ............................................. G01H 5/00
[52] U.S. Cl. ................... 73/597; 73/DIG. 1; 73/DIG. 4; 73/866
[58] Field of Search ....................... 73/597, 570, DIG. 4, 73/DIG. 1, 866; 310/800

[56] References Cited

U.S. PATENT DOCUMENTS 4,877,988  10/1989  McGinniss et al. .................... 310/306

*Primary Examiner*—Hezron Williams
*Assistant Examiner*—Richard A. Moller
*Attorney, Agent, or Firm*—Lyon & Lyon LLP

[57] ABSTRACT

The present invention relates to methods for determining the uniformity of the piezoelectric effect throughout a piezoelectric material using the time-of-flight of an acoustic wave through the material as a gauge of that uniformity.

35 Claims, 4 Drawing Sheets

(1 of 4 Drawing Sheet(s) Filed in Color)

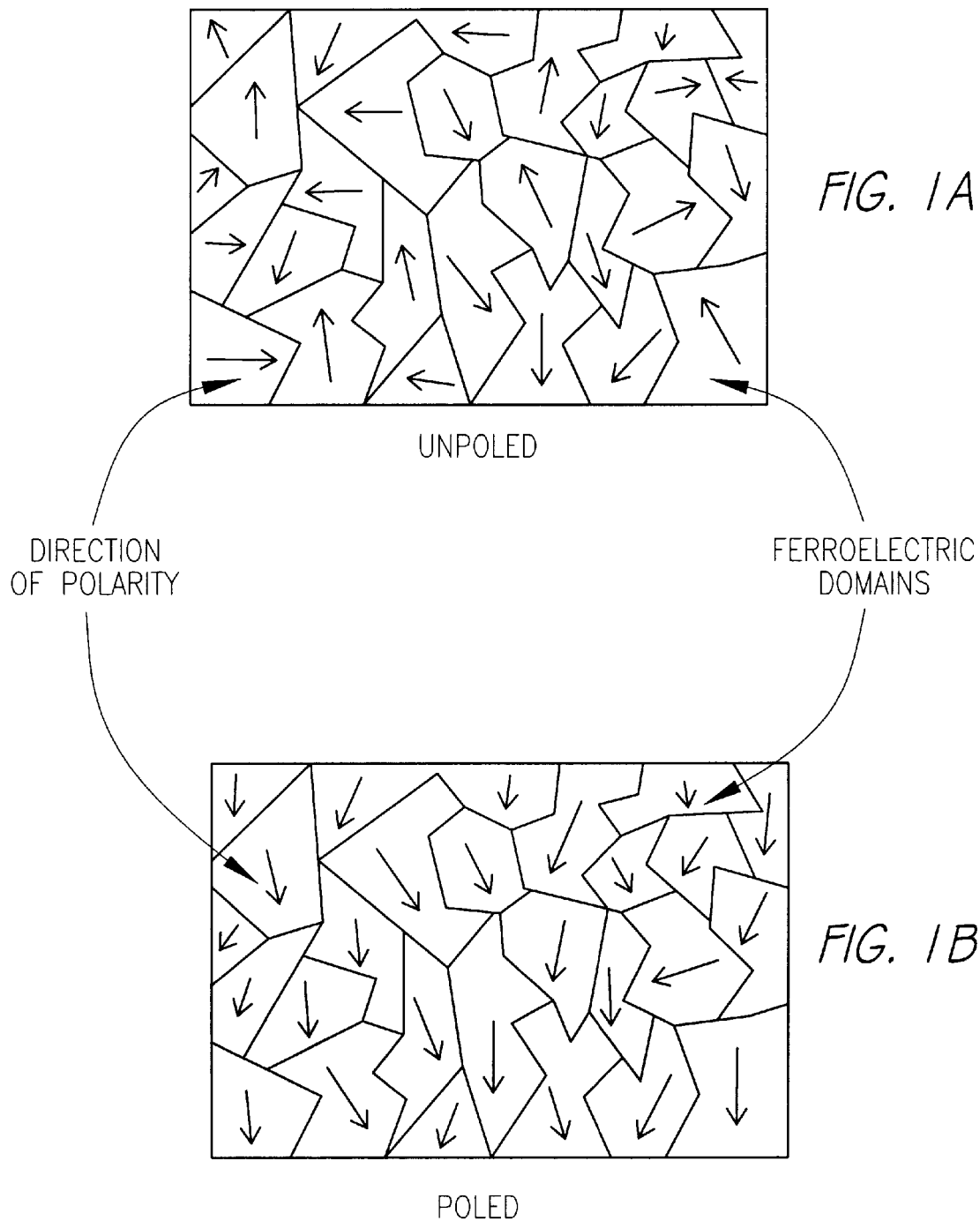

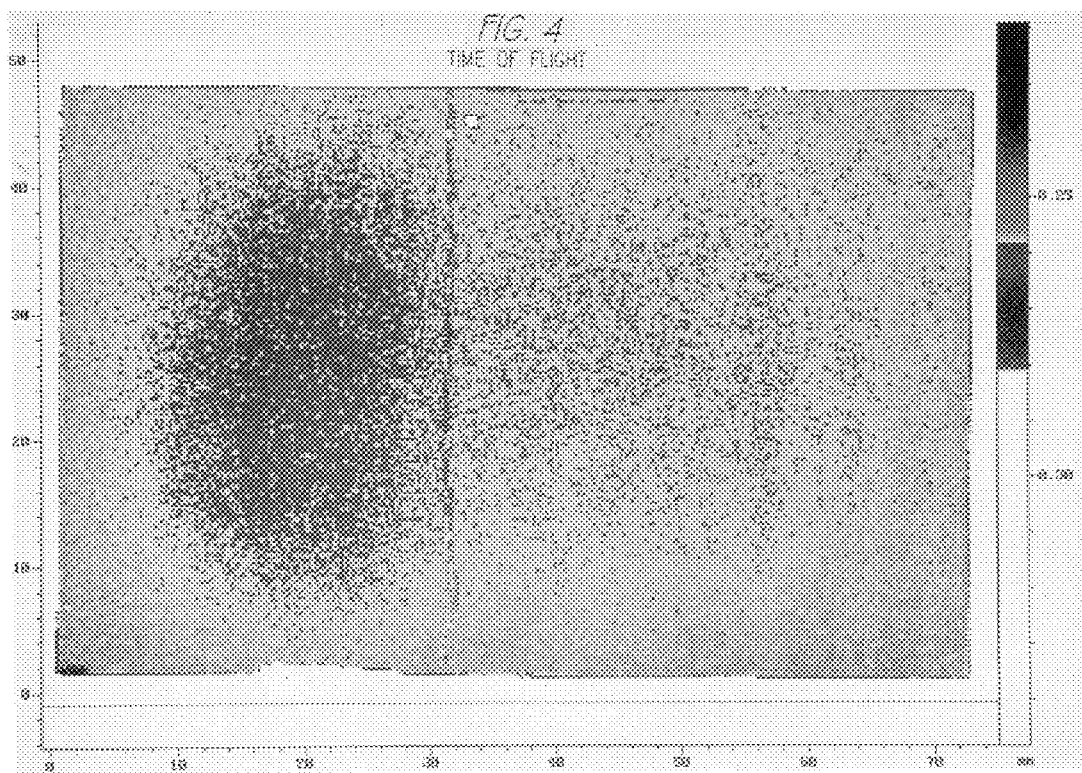

METHOD FOR EVALUATING PIEZOELECTRIC MATERIALS

COLOR DRAWINGS

The file of this patent contains one drawing executed in color. Copies of this patent with color drawing will be provided by the Patent and Trademark Office upon request and payment of necessary fees.

FIELD OF THE INVENTION

This invention relates generally to the field of material science, more particularly to materials analysis and most particularly to the evaluation of piezoelectricity in a piezoelectric material.

BACKGROUND OF THE INVENTION

Piezoelectricity or, synonymously, the piezoelectric effect was discovered by Pierre and Jacques Curie in 1880. The effect is manifested by the appearance of an electric potential across the faces of some materials when those materials are placed under pressure. Conversely, when a piezoelectric material (PEM) is subjected to an electric field, physical stresses are created in the material and it distorts, a phenomenon known as the converse piezoelectric effect.

Among the materials exhibiting the piezoelectric effect are crystalline substances whose unit crystal structure lacks a center of symmetry and polycrystalline substances which have been placed in a polarized state, called piezoelectric ceramics.

An example of a PEM is the piezoelectric ceramic PZT, an amalgam of lead, zirconium and titanium. Other PEMs include, without limitation, piezoelectric polymers and polymer-ceramic composites.

PEMs have many diverse uses. For example and without limitation, PEMs are used in thin film capacitors, non-volatile ferroelectric semi-conductor memory, optical wave guides, optical memory and display, SAW (surface acoustic wave) devices, medical ultrasound applications, gas ignitors, displacement tranducers, accelerometers, transformers, impact printer heads and ink-jet printer heads.

The piezoelectric effect involves a complex interaction of electrical and mechanical properties of a material; up to 18 piezoelectric coefficients may be necessary to fully quantify piezoelectricity in a particular PEM. Yet, in many of the above applications, it is necessary that the piezoelectric effect be relatively homogeneous throughout the volume of the PEM being employed to be effective in that particular application; thus, some level of quantification is required. To accomplish this quantification, the usual source of methodology is the IEEE (Institute of Electrical and Electronic Engineers) Standard on Piezoelectricity, IEEE Std. No 176-1987 (incorporated by reference as if fully set forth herein) which contains test methods for determining various piezoelectric constants in a given PEM.

The present IEEE standard, however, does not adequately characterize piezoelectricity for certain applications. An example, without limitation, of such an application is the drop-on-demand ink-jet printer head. In this application, an electrical signal applied to a piezoelectric ceramic wafer causes deformation in the wafer resulting in expulsion of ink from an ink chamber formed within the wafer. Recently developed drop-on-demand ink-jet printer heads may contain as many as 128 such ink chambers closely packed into a single piezoelectric ceramic wafer, each chamber being capable of being individually deformed by application of a localized electric field. If the amount of deformation of the PEM in the immediate vicinity of each of the 128 ink chambers is not substantially the same as that in the immediate vicinity of each of the other ink chambers, the amount and velocity of ink delivered from each ink chamber will not be the same and unacceptable variations in the resultant print will result. The situation is exacerbated when the ink-jet printer is a color printer. In a color printer, the amount and placement of ink expulsed from the ink chambers is directly related to the ultimate color of the image obtained; minute variations in the amount of ink and placement of drops ejected from each chamber can lead to poor color image reproduction.

To avoid the preceding problem, it would be desirable to be able to determine the uniformity of the piezoelectric effect throughout the volume of the piezoelectric ceramic wafer from which a drop-on-demand ink-jet print head is to be manufactured to assure that an electric field applied in the vicinity of each of the closely packed ink chambers within the wafer will produce the same amount of deformation in that chamber as in each of the other chambers thereby assuring a uniform delivery ink. The IEEE methods, however, afford only average values of the piezoelectic constants in a PEM, leaving open the possibility of localized differences which might, in the case of the ink jet printer head, for example, result in inconsistency in the amount of ink ejected from the individual ink chambers and thus poor print quality and/or color reproduction.

Thus, there is a need for a method for evaluating the uniformity of the piezoelectric effect throughout a PEM to determine whether it is sufficiently uniform for the intended end use of the PEM. The present invention provides such a method.

SUMMARY OF THE INVENTION

Lack of a center of symmetry in the unit cells of a crystalline material is essential for the material to exhibit piezoelectricity; however, it is not sufficient. That is, man-made ferroelectric materials in which the unit crystals do lack a center of symmetry, such as, without limitation, the aforementioned PZT, do not show any net piezoelectric effect as initially manufactured. This is because, as manufactured, the grains within PZT are in a random orientation. This results in the crystalline PZT having no net polarity and therefore being incapable of exhibiting piezoelectricity. Another step is required in the manufacturing process to instill piezoelectricity in the PZT. This step is known as "poling." Poling is achieved by the application of an electric field to the PZT with a field strength larger that the coercive field strength of PZT. Poling results in the growth of the ferroelectric domains within the grains more favorably aligned with the applied field at the expense of those domains not favorably aligned (FIG. 1). When the external electric field is removed, a net polarization, called remnant polarization, remains in the PZT. The remnant polarization is oriented in the direction of the removed external field. The remnant polarization results in the poled ferroelectric material exhibiting a net piezoelectric effect.

As used herein, a "ferroelectric material" refers to a polycrystalline material which has the requisite lack of symmetry in its unit cells to be piezoelectric but in which the ferroelectric domains are randomly distributed so that, as noted above, the material cannot yet exhibit a net piezoelectric effect. The abbreviation "FEM" will be used herein to refer to a ferroelectric material.

A ferroelectric domain is a region of like polarity within a ferroelectric material (see FIG. 1).

A "PEM" refers to a ferroelectric material which has been poled so that the ferroelectric domains are aligned sufficiently to impart a net polarity; i.e. remnant polarization, to the material which then is capable of piezoelectricity. The abbreviation "PEM" will be used herein to refer to a poled piezoelectric material.

The coercive field is the electrical field strength at which polarization of a PEM is reversed.

The remnant polarization in a PEM is a relatively stable phenomenon; the aging rate for remnant polarization is often given in percent loss per decade.

One of the constants associated with piezoelectricity is the piezoelectric charge coefficient or "d-constant." The d-constant for the piezoelectric effect is defined as the amount of strain developed in the material per unit of electrical field applied; i.e.:

$$d = \text{Strain developed/Applied Field} \quad\quad 1$$

The strain developed, of course, is related directly to the amount of deformation which will occur in the PEM when an electric field is applied to the material. For applications in which motion or vibration of the PEM is required, a high d-constant is desirable; i.e., a high degree of strain relative to the field applied is desired since this will result in a powerful vibratory motion. Furthermore, in applications such as the previously discussed drop-on-demand ink-jet printer head, it is highly desirable that the d-constant be uniform throughout the volume of the PEM so that the strain developed in the vicinity of each of the ink chambers will be substantially the same for a given applied field.

The d-constant of a PEM is directly proportional to the remnant polarization of the PEM. Thus, if the remnant polarization is uniform throughout the volume of a PEM, then it can be expected that the d-constant and, therefore, the strain developed per unit charge applied will likewise will be uniform throughout the volume of the PEM.

By "uniform", "uniformity", "substantially the same", "essentially the same" and words to that effect when referring to the d-constant in a particular PEM, the remnant polarization in the material, the physical dimensions of the material or the time-of-flight of an acoustic wave through the material (discussed below) is meant that, throughout the volume of a PEM, a variation of no more than from about 0% to about 20%, preferably from about 0% to about 8%, most preferable from about 0% to about 3% in that characteristic exists in that PEM.

As used herein, the term "about" means that the numerical value of the parameter which is modified by the word "about" may vary by ±10% from the value given.

The speed of acoustic waves in a solid material is affected by the polarity of that material. Furthermore, the speed of an acoustic wave in such material is inversely proportional to the degree of polarization; that is:

$$\frac{V_p}{V_{up}} = \frac{1}{\sqrt{1 - 2QP_i}} \quad\quad 2$$

wherein $V_p$ is the speed of an acoustic wave in a poled material; i.e., a material having a remnant polarization; $V_{up}$ is the speed of the acoustic wave in the unpoled (ferroelectric) material; Q is a material constant and $P_i$ is the remnant polarization.

Of course, other constants associated with piezoelectricity can have an effect on the speed of an acoustic wave in a PEM; however, the speed of an acoustic wave is particularly sensitive to the degree of net or remnant polarization in the PEM. Thus, by measuring the speed of an acoustic wave in a PEM, the amount of remnant polarization can be determined. Since the remnant polarization is proportional to the d-constant, a uniform acoustic wave speed throughout a PEM which translates to a uniform remnant polarization likewise indicates a uniform d-constant. A uniform d-constant in a PEM in turn indicates that, pursuant to Equation 2, the PEM will exhibit a uniform converse piezoelectric effect when subjected to an electric field.

Thus, in one aspect of this invention, an acoustic wave is applied to a point on one surface of a PEM, which surface, for the purposes of this discussion shall arbitrarily be referred to as the "front surface." The acoustic wave is then intercepted by a detector located at the side of the material which forms a plane opposite and substantially parallel to the surface to which the acoustic wave is applied, which opposite surface shall, for the purposes of this discussion, be arbitrarily referred to as the "back surface" (FIG. 2). By stating that the surfaces are "arbitrarily" designed is meant that the surfaces are freely interchangeable; i.e., the acoustic wave could as easily be applied to the "back" surface and detected at the "front" surface.

By "substantially parallel" is meant that the PEM is of uniform thickness, front to back.

The time-of-flight (TOF) through the PEM of the acoustic wave is then determined. By "time-of-flight" is meant the time it takes the acoustic wave to travel from a source through a PEM to a detector. In another embodiment of this invention, the TOF is measured as the time it takes for an acoustic wave to travel from a source through a PEM to the back surface of the PEM and from there back through the PEM to the front surface where it is detected. As long as all TOFs being compared are of the same kind; i.e., front-to-back or front-to-back-to-front, the ability of the TOF to predict the uniformity of the piezoelectric effect in the PEM is the same.

The above procedure is repeated at a plurality of points on the PEM. The TOFs at the plurality of points on the PEM are then compared to one another. Uniformity in the TOF of the acoustic wave at two or more points can be interpreted, pursuant to the above analysis, as an indication of the uniformity of the d-constant at those points and thus of the uniformity of the piezoelectric effect at those points. Thus, when TOFs have been determined at a sufficient number of points throughout the PEM, the uniformity of the piezoelectric effect throughout the PEM, as manifested by the uniformity of the d-constant, can be determined. In a presently preferred embodiment of this invention, variations in the TOF throughout the target PEM are visualized as different colors on a cathode ray tube (CRT) display.

Of course, if the PEM is not of uniform thickness, it is still possible to perform this analysis by including a correction factor based on actual measurement of the thickness of the material at each point of measurement of the TOF of the acoustic wave to normalize the results obtained. Such could be accomplished, for example, by employing laser techniques well-known in the optics field for measuring surface variations.

In another aspect of this invention, rather than applying the acoustic wave at discrete points on the front surface of the PEM, the acoustic wave may be scanned continuously across the front surface of the PEM, the detector at the back surface of the material being scanned in synchronization with the source to detect the continuously propagated acoustic wave.

By "being in synchronization" is meant that the position of the detector during scanning in relation to the position of the source of the acoustic wave during scanning remains constant.

In a further aspect of this invention, the acoustic wave is focused by an acoustic lens. By "focused" is meant that the acoustic waves generated by a source converge at a focal point. The focal point of the acoustic wave is the methods of this invention is the back surface of the PEM where that surface interfaces with the external environment (FIG. 3a). In this embodiment the acoustic wave travels through the PEM, reflects off the back surface and travels back through the PEM to the front surface where it is detected by a detector.

In yet another aspect of this invention, the methods provided herein can be used to obtain a quantitative measurement of the remnant polarization induced in an FEM simply by determining the TOF of an acoustic wave in the FEM prior to poling and comparing that with the TOF in the PEM created by poling the FEM.

It is a further aspect of this invention that the source of the acoustic wave is coupled to a surface of the PEM by a coupling liquid that interfaces between the source and the PEM. Likewise, it is an aspect of this invention that the detector is coupled to a surface of the PEM by the coupling liquid (FIG. 2, FIG. 3).

It is also an aspect of this invention that, when a focused acoustic wave is employed and the acoustic wave is detected at the same surface; e.g., the "front" surface, to which it is applied, in which case the source of the acoustic wave may also act as the detector. (FIG. 3b).

In a particularly preferred embodiment of this invention, the methods described herein are carried out using scanning acoustic microscopy (SAM).

The file of this patent contains at least one drawing executed in color. Copies of this patent with color drawing(s) will be provided by the Patent and Trademark Office upon request and payment of the necessary fee.

BRIEF DESCRIPTION OF THE FIGURES

The figures shown herein are offered by way of example only and are not to be construed as limiting the scope of this invention in any manner.

FIG. 1a shows a schematic representation of an unpoled ferroelectric ceramic and the direction of polarity of individual ferroelectric domains therein. The polarities of the domains are random resulting in the material having no net polarity and, therefore, being incapable of exhibiting a piezoelectric effect.

FIG. 1b shows a schematic representation of the same ferroelectric ceramic as that shown in FIG. 1a but after poling. As can be seen, the individual ferroelectric domains have become oriented predominantly in one direction so that the ferroelectric ceramic has a net polarity and is capable of exhibiting a piezoelectric effect.

FIG. 4 shows a palette of colors chosen to display time-of-flights of acoustic waves.

DETAILED DESCRIPTION OF THE INVENTION

The frequency of the acoustic wave for use in the methods of this invention is selected from a range of from 100 Hz to 8 Ghz, preferably from about 5 Mhz to about 2 GHz, most preferably from about 5 MHz to about 200 MHz. Lower frequency waves are chosen for their ability to permeate thicker materials; however, this occurs at the expense of resolution; i.e., at lower frequencies the ability to resolve differences in time-of-flight is lessened.

The acoustic wave can be is generated by a wide variety of sources such as, without limitation, a piezoelectric tranducer. Likewise the detector of the acoustic wave can be selected from a variety of acoustic detectors such as, without limitation, a second piezoelectric transducer. The source can generate the acoustic wave as a continuous wave or in pulses.

Figure 2A:
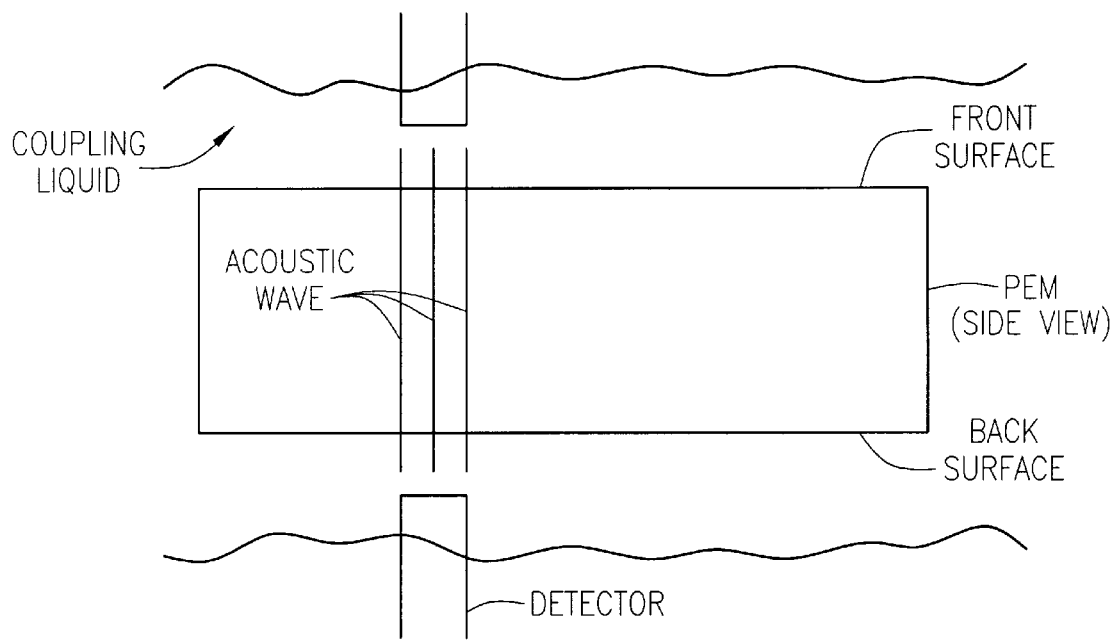
FIG. 2a shows a schematic representation of a side view of a PEM and a source of acoustic waves positioned at the front face of the PEM which source is coupled to the PEM by a coupling fluid. A detector is shown positioned at the back face of the PEM and is likewise coupled to the PEM by a coupling liquid. Lines representing acoustic waves are shown going through the PEM from the source to the detector.
Figure 2B:
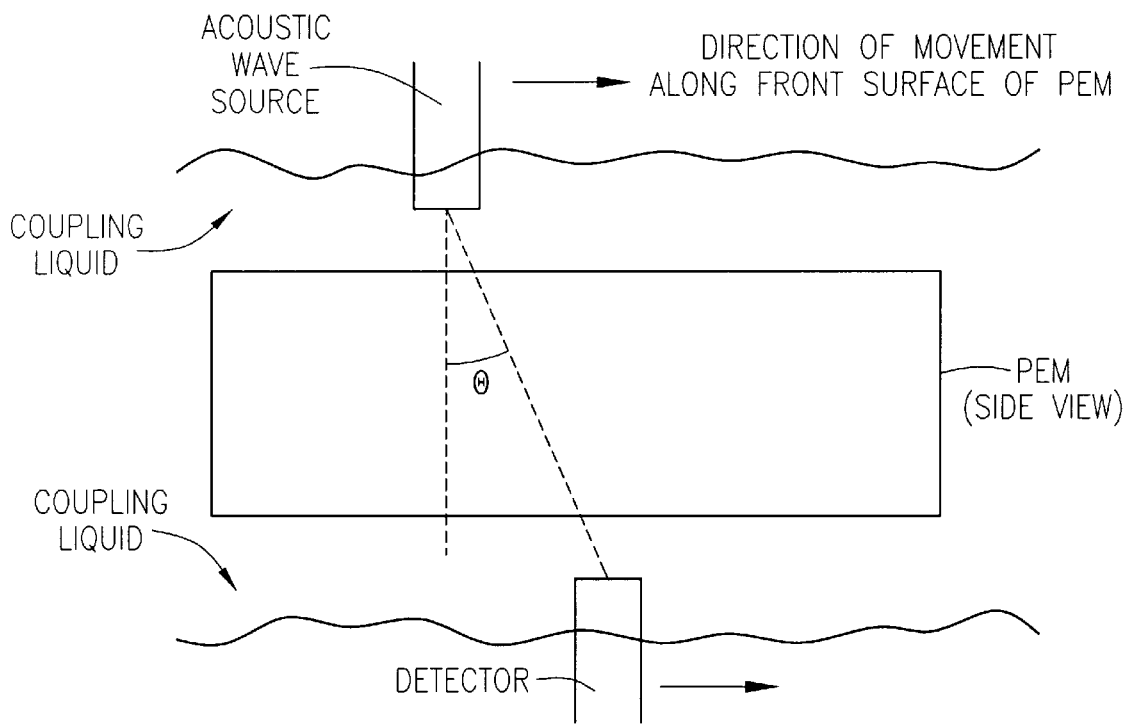
FIG. 2b shows the angle θ which must be maintained between the position of the source and the position of the detector as the source and detector scan across the surfaces of the PEM.

In one aspect of this invention, an acoustic wave is generated at the front surface of a PEM by a source which is coupled to the front surface of the PEM. The acoustic wave is then applied to a point on that front surface. The acoustic wave travels through the PEM to the back surface where it is detected by a detector, which detector is coupled to the back surface of the PEM (FIG. 2).

By "applied" to a point on the front surface is meant that the acoustic wave is directed against the front surface of the PEM such that the wave impinges on the front surface of the PEM and propagates into and through the material to the back surface.

Figure 3A:
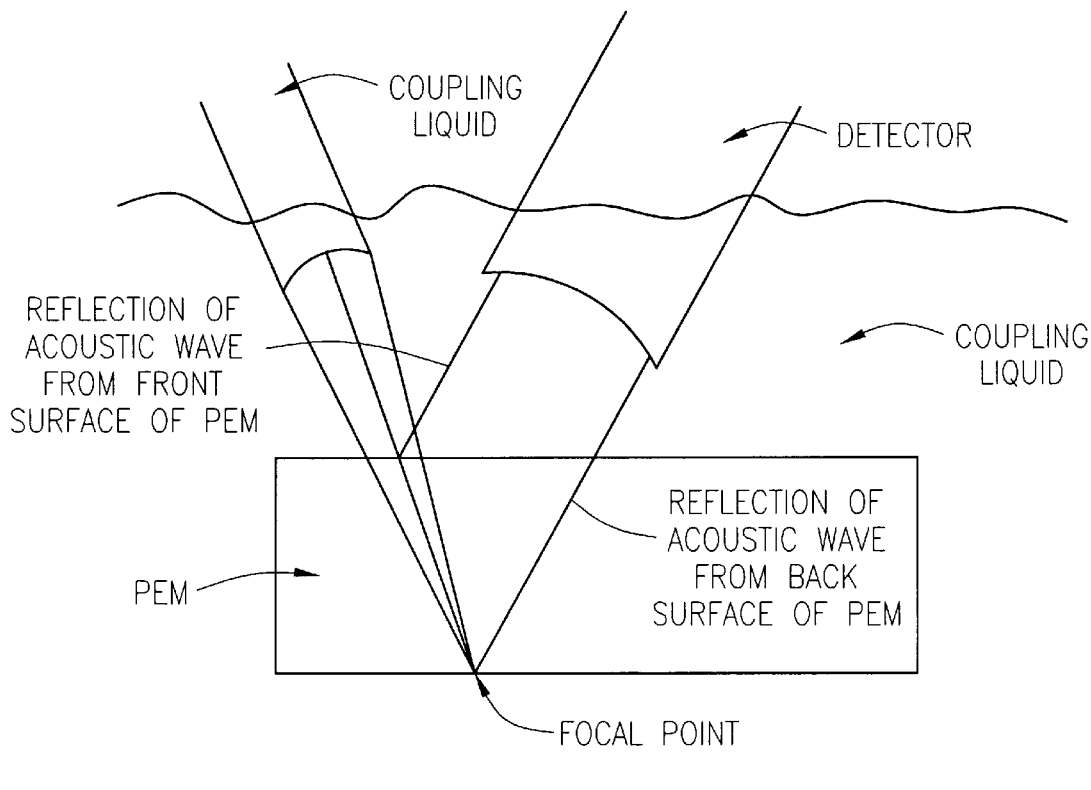
FIG. 3a shows a schematic representation of a source which focuses an acoustic wave; the wave is shown focused on the interface of the back surface and the external environment. The paths of the acoustic wave are also shown with a portion of the wave being depicted as reflecting off the front surface and then to the detector while the remainder of the wave passes through the PEM to the back surface and reflects off that surface, back through the PEM to the detector.

By being "coupled" to either the front or back surface of the PEM is meant that a coupling liquid, q.v., infra, is in contact both with the source and the front surface of the PEM and the detector and the back surface of the PEM (FIG. 3).

The TOF of the acoustic wave in the PEM from the point of application on the front surface to the point of detection on the back surface is then determined. The process is repeated at a plurality of other points on the front surface and detected at a corresponding plurality of points on the back surface.

By "a corresponding plurality of points in the back surface" is meant that, for each point of application on the front surface, there is one point of detection on the back surface. The angle between the point of application and the point of detection is constant for each point of application and its corresponding point of detection. When measured as the angle of a line drawn from the point of application on the front surface to the point of detection on the back surface with a line drawn from the point of application orthogonally through the PEM, the angle is between 0° and 45°, preferably 0° and 10°, most preferably between 0° and 1° (FIG. 2).

Figure 3B:
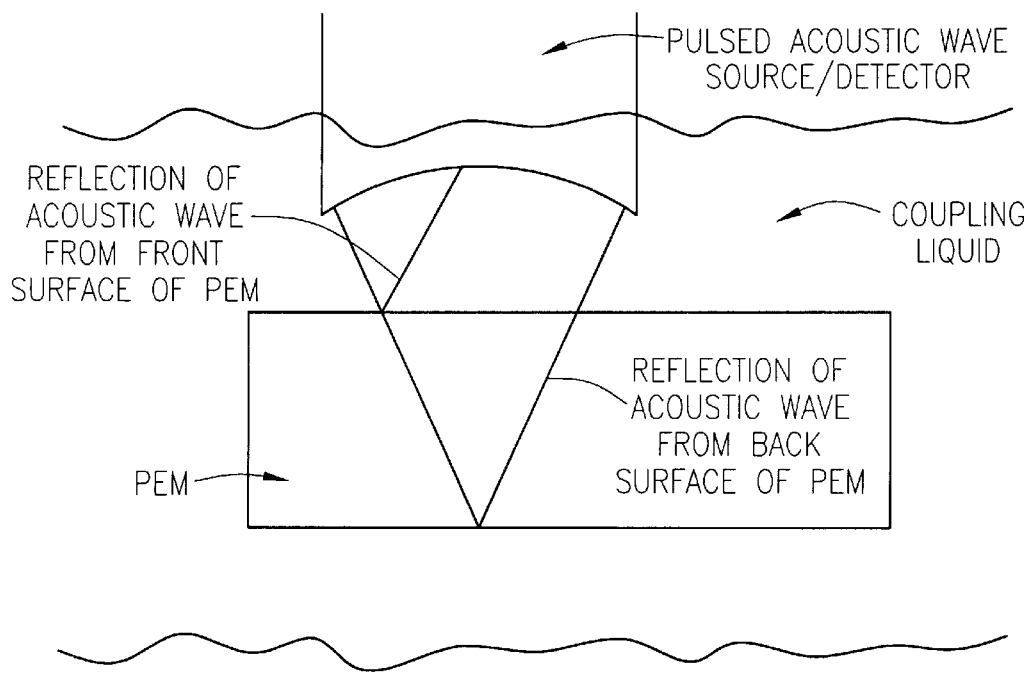
FIG. 3b shows a schematic representation of an embodiment of this invention is which the source generates acoustic waves in pulsed bursts. In this embodiment, the source can also act as a detector between pulses. The source detects both the reflection off the front surface and the reflection off the back surface of the PEM.

In a presently preferred embodiment of this invention, the acoustic wave is generated at the front surface of the PEM by a source which is coupled to the front surface by a coupling liquid and which focuses the acoustic wave on a point on the back surface of the PEM where the back surface interfaces with the external environment. The acoustic wave is then applied as a pulse to a point on the front surface. A portion of the acoustic wave is reflected from the front surface to the source which, between generation of pulsed acoustic waves, acts as a detector of reflected acoustic waves. The remainder of the acoustic wave travels through the PEM to the focal point on the back surface. There, the acoustic wave is again reflected, back through the PEM to the source which is still acting as a detector. In this mode the difference between the time the source/detector detects the wave reflected from the front surface and the time the source/detector detects the wave reflected from the back surface is twice the time of flight of the acoustic wave through the PEM. This embodiment is depicted in FIG. 3b.

The point of application of the acoustic wave to the front surface of the PEM covers a surface area of from about 5 $\mu$m to about 500 $\mu$m, preferably from about 10 $\mu$m to about 100 $\mu$m, most preferably from about 20 $\mu$m to about 50 $\mu$m in diameter.

As noted previously, the acoustic wave can be applied to the front surface of the PEM as a continuously generated wave or in pulsed bursts.

In a preferred embodiment of this invention, the acoustic wave is applied in pulsed bursts, the points of application of such bursts being from about 0.1 mm to about 100 mm, preferably from about 0.1 to about 10 mm, most preferably from about 0.1 mm to about 1.0 mm apart.

In another preferred embodiment, the source of the acoustic wave is coupled to the front surface by a coupling liquid which is in contact with the source of the acoustic wave and the front surface of the PEM. In this embodiment, the detector is likewise coupled to the PEM by a coupling liquid which is in contact with both the detector and the PEM.

The coupling liquid can be, without limitation, water or an organic liquid such as, without limitation, a $C_6$ to $C_{20}$ alkyl hydrocarbon, a $C_1$ to $C_8$ alkyl ester, a $C_2$ to $C_8$ alkyl ether, a $C_1$ to $C_8$ alkyl ketone, a $C_1$ to $C_4$ alkyl sulfoxide, a $C_6$ to $C_{10}$ aromatic hydrocarbon or the like.

As used herein, "alkyl" refers to a straight or branched carbon chain. The alkyl group may be unsubstituted or substituted with one or more halo groups.

A halo group refers to a fluorine, chlorine, bromine or iodine.

An "aromatic hydrocarbon" refers to a monocyclic or polycyclic all carbon ring compound having a fully conjugated pi-electron system. The aromatic hydrocaron may be unsubstituted or substituted. When substituted, the substituent group is selected from the group consisting of alkyl, halo and hydroxy.

A hydroxy group refers to an —OH group.

An "alcohol" refers to ROH wherein R is alkyl.

An "ester" refers to RC(=O)OR' wherein R and R' are independently alkyl.

An "ether" refers to ROR' wherein R and R' are independently alkyl.

A "ketone" refers to RC(=O)R' wherein R and R' are independently alkyl.

A "sulfoxide" refers to RS(=O)$_2$R' wherein R and R' are independently alkyl.

In a preferred embodiment of this invention, the coupling liquid is water.

The coupling liquid may be heated or cooled to a temperature of from about 1° above the freezing point of the chosen liquid to about 1° below the boiling point of that liquid. Preferably, the temperature of the coupling liquid is maintained at from about 20° C. to about 60° C., most preferably from about 22° C. to about 25° C.

In a further aspect of this invention, an acoustic wave is generated by a source which is coupled to the PEM by a coupling liquid. The acoustic wave is then transmitted to the front surface of the PEM by the coupling liquid. The wave continues through the PEM to the back surface where it is transmitted to a detector by a coupling liquid. The detected wave may then be displayed directly on an oscilloscope, from which the TOF through the PEM at the point of application can be determined or, in a presently preferred embodiment, the time-distance relationships produced by the polarity of the PEM are sent to a computer where they are converted by a computer program to a format amenable to display on a computer screen. For example and without limitation, the TOF at each point of measurement over the surface of the PEM can be converted by a computer program to a brightness level of a spot of light. The spot of light can then be displayed on a cathode ray tube (CRT) screen at a point on the CRT that corresponds to the point of application of the acoustic wave to the PEM. A pattern of spots can be generated in this manner by determining the TOF at intervals, such as those discussed above, over the surface of the PEM, converting each TOF to a spot brightness and then displaying the pattern of spots on the CRT. The uniformity in brightness of the complete pattern of spots will be a measure of the uniformity of TOFs throughout the PEM and, thus, of the uniformity of the piezoelectric effect in the target PEM.

In a presently particularly preferred embodiment of this invention, the TOFs are converted by the computer program to spots of different color. The color palette, i.e., the colors chosen for different TOFs is selected based on the range of TOFs expected in the target PEM as determined by the thickness of the PEM and the thickness tolerance (i.e, how uniform the thickness of the PEM is (Example 1, below describes this aspect of this invention in detail). These colored spots, each representing a particular TOF, are then displayed on a color CRT. The pattern of color produced provides a graphic representation of the uniformity of the piezoelectric effect throughout the volume of the PEM. The pattern on the computer screen can be sent to a printer to provide a permanent record of the results of the test. FIG. 4 shows the results of a test performed on a PEM in which differences in the piezoelectric effect were purposely induced.

If a continuous wave source is employed, the continuous data generated may be broken down by an appropriate computer program into individual measurements, the time between such measurements being selected such that the distance between measurements corresponds to the distance between the point measurements in the pulsed wave procedure.

As noted previously, it is a presently particularly preferred embodiment of this invention that the methods described herein are carried out using SAM. For a detailed description of SAM, see Yu and Boseck, *Review of Modern Physics*, 67:4 1995 (which is incorporated by reference as if fully set forth herein). When using SAM, a focused acoustic wave, as described above, is used. The focussed acoustic wave is generated by a crystal rod into one end of which is a polished a concave hemispherical surface, which constitutes an acoustic lens. The acoustic lens end of the rod is placed in contact with a coupling liquid which, as described above, is also in contact with the front surface of a target PEM thus coupling the acoustic lens to the PEM. The other end of the crystal rod is placed in contact with a source of acoustic waves such as, without limitation, a piezoelectric transducer. In this mode, the detector may be located at the back surface of the PEM in contact with the coupling liquid that is also in contact with the back surface of the PEM. The detector intercepts that portion of the focussed acoustic wave that continues on through the back surface of the PEM (transmission SAM). Preferably, however, the detector is located at the front surface of the PEM and is in contact with the coupling liquid which is also in contact with the PEM. The acoustic wave is then focussed at the interface of the back surface with the coupling liquid. A portion of the acoustic wave is reflected from the front surface of the PEM and is detected by the detector. The remainder of the acoustic wave travels through the PEM and is partially reflected from the focal point at the back surface back through the PEM to the front surface where it is detected by the detector. The TOF is then determined as the difference between the time of detection of the acoustic wave reflected from the front surface and the time of detection of the acoustic wave reflected from the back surface of the PEM (reflection SAM).

In a further presently preferred embodiment, SAM is used in pulse mode, as described above. While, in this embodiment it is still possible to employ a separate detector and intercept the pulsed acoustic wave at the back surface of the PEM (transmission SAM), in a preferred embodiment, the source serves as both the generator of the acoustic wave and the detector of the echo of the acoustic wave; that is, SAM is used in the reflection mode. In this mode, a pulse of acoustic energy is produced by the SAM source then, between pulses, the echoes from the front and back surfaces are intercepted by the source, which acts as a coherent detector. After one pulse has been detected, another pulse is produced and so on.

In a further preferred embodiment of this invention, SAM can be used to determine the actual amount of remnant polarization in a PEM and thereby the amount of piezoelectric effect which can be expected from an FEM after poling simply by applying a method of this invention to an FEM prior to poling, then applying it to the PEM created by poling of the FEM and comparing the TOF of the acoustic wave in the FEM with that in the PEM.

Of course, since an acoustic wave cannot propagate through a void, the methods described herein can be employed to detect physical defects in a PEM as well as determining the uniformity of the piezoelectric effect therein. That is, since the acoustic wave will not propagate through voids, cracks, holes, etc., there will be no reflection from the back surface and thus no TOF measurement. Without a TOF from which to develop a brightness level for a spot of light or a colored spot of light, no spot of light or color will appear in the corresponding location on the CRT display. This absence of dots or absence of color will then correspond to a physical defect in the PEM.

In a preferred embodiment of this invention, the PEM is a peizoelectric ceramic wafer that is to be manufactured into a drop-on-demand printer head assembly.

EXAMPLES

The following is presented by way of example only of the methods of this invention and is not to be construed as limiting the scope of this invention in any manner whatsoever.

Example 1

A Sonix HS-500 Scanning Acoustic Microscope was used in the following experiment. The following setting were employed for the user-selected parameters of the instrument:

| | Overall instrument feature parameters: | |
|---|---|---|
| 1) | Water Path | 8.779 $\mu$m |
| 2) | Package Material Velocity | 4.7 mm/$\mu$m |
| 3) | Die velocity | N/A |
| 4) | Voids in depth image | No |
| 5) | Measure of TOF to | Edge |
| 6) | % Delam only in Lead Frame | No |
| 7) | Save Peak Amplitude Image | Yes |
| 8) | Save TOF Image | Yes |
| 9) | Save Phase Inversion Image | No |
| 10) | Save Void Image | No |
| | Pulser/Receiver Setup | |
| 1) | Attenuation: | 8 dB |
| 2) | Frequency: | High |
| 3) | Gain: | High |
| 4) | Pulsing: | On |
| 5) | Damping: | 3.6 |
| 6) | Transmission Mode: | Pulse/Echo |
| 7) | Trigger: | Ext. |
| | Scan Setup | |
| 1. | Scan Data Points: | 2107 (0.035052 mm) [148 (0.499364 mm)] |
| 2. | Step Points: | 1359 (0.035052 mm) [96 (0.499364 mm)] |
| 3. | Acceleration: | 800.0 mm/sec$^2$ |
| 4. | Velocity: | 200.6 mm/sec$^2$ |
| 5. | Bi-directional: | On |
| 6. | Tray Scan: | Off |

| Palette Specifications for TOF | | | | | |
|---|---|---|---|---|---|
| | Hinge | Position | Intensity | Hue | Saturation |
| 1) | 1 | 100.0% | 0% | None | 0 |
| 2) | 2 | 79.76% | 100% | Red | 100% |
| 3) | 3 | 77.73% | 100% | Yellow | 100% |
| 4) | 4 | 76.52% | 100% | Blue | 100% |
| 5) | 5 | 51.82% | 100% | Green | 100% |
| 6) | 6 | 51.42% | 100% | None | 0 |

A PEM wafer measuring 70 mm long X 45 mm wide X 0.596 mm thick was completely submersed in deionized water in a rectangular metal pan fitted with supporting elements which fit along the two long edges of the wafer and which were approximately 1 mm in width such that the entire thickness of the wafer fit within the width of the supporting element. In this manner echoes from the support element won't exist for most of the scanned area of the wafer.

The acoustic wave source, a piezoelectric transducer, was then submersed in the water and brought to with 1mm of the front (or top) surface of the wafer. The transducer was then focused on back (or bottom) surface of the wafer where it intersected with the water. The signals of interest were the first echoes from the front and the back surfaces. Other signals created by the two surfaces which were multiples of the primary signals were filtered out.

When focused, the front surface echo was recorded at 10 milliseconds. The back surface echo trailed the front surface echo by approximately 250 nanoseconds (ns).

A scan was then run using the parameters described above. The scan took approximately 2½ minutes.

The PEM wafer has a thickness tolerance of 0.5 mil (12.5 microns). Assuming that the wafer were completely poled, it would show an acoustic velocity of 4.7 mm/$\mu$sec and, given the preceding tolerance, TOFs in the range of 248 to 258 ns would be expected. On the other hand, if the wafer were completely unpoled, the acoustic velocity would be 4.4 mm/$\mu$s which translates to TOFs in the range of 265–276 ns. Thus, any TOF over 258 ns in the test wafer would indicate imcomplete poling.

To test the ability of the method of this invention to detect and display in a manner conducive to human interpretation indications of imperfect poling, the left hand side of the test wafer was purposely partially depoled by heating. The wafer was then subjected to analysis using the colored spot production method of this invention. A palette of colors was chosen to display TOFs such that a relatively bright easily discernible color, yellow, was used to represent the upper limit of TOFs expected for the fully poled PEM; i.e., TOFs of 258 ns. A *-sharply contrasting color, blue, was selected to represent the lower limit of TOFs which would indicate imperfect poling of the PEM. The result is shown in FIG. 4 which is a print out of a computer screen (CRT) generated during the experiment. The color palette selected is shown in the far right hand column of FIG. 4. As can be seen, the color pattern on the right hand portion of the print-out, which corresponds to the right hand side of the PEM, is quite uniform and consists of color spots of from orange to yellow. These colors represent TOFs in the range of 0.248 $\mu$s to 0.258 $\mu$s (248–258 ns) which is the range calculated to correspond to complete poling. On the other hand, only an occasional blue spot, indicative of a longer TOF and therefore incomplete poling, is in evidence on the right hand side of the print-out. In contrast, the left hand side of the print out is predominantly blue which means that the TOFs in the left hand side were generally longer which in turn indicates that the left hand side of the wafer was incompletely poled compared to the right hand side. Thus, it can be seen that this invention provides a simple, visually vivid method for determining the uniformity of TOFs and, therefore, of the piezoelectric effect in a PEM.

CONCLUSION

Thus, it will be appreciated that the methods of the present invention provide a powerful new method by which to study and evaluate piezoelectricity in ferroelectric substances, a method which will find particular use in those applications of piezoelectricity in which uniformity of the piezoelectric effect throughout the volume of a PEM is required.

Although certain embodiments and examples have been used to describe the present invention, it will be apparent to those skilled in the art that changes to the embodiments and examples shown may be made without departing from the scope and spirit of the invention.

Other embodiments are within the following claims.

What is claimed:

1. A method for determining the uniformity of the piezoelectric effect in a piezoelectric material (PEM) comprising:
    applying an acoustic wave to a plurality of points on a front surface of said PEM;
    detecting said acoustic wave at a plurality of points on a back surface of said PEM, each of said plurality of points of detection on said back surface corresponding to one of said plurality of points of application on said front surface of said PEM;
    determining a time-of-flight of said acoustic wave from each of said plurality of points of application of said acoustic wave to said front surface of said PEM to each of said plurality of corresponding points on said back surface of said PEM; and,
    determining said uniformity of said piezoelectric effect in said PEM by comparing each said time-of-flight at each said plurality of corresponding points on said back surface with said time-of-flight at each other of said plurality of corresponding points on said back surface of said PEM.

2. The method of claim 1 wherein:
    said acoustic wave has a frequency of from 100 Hz to 8 GHz;
    each of said plurality of points of application on said front surface covers a surface area of from about 5 $\mu$m to about 500 $\mu$m in diameter; and,
    said plurality of points of application of said acoustic wave to said front surface of said PEM are from about 0.1 mm to about 1 cm apart.

3. The method of claim 1 wherein said determining said uniformity of said piezoelectric effect comprises a cathode ray tube (CRT) display.

4. The method of claim 2 wherein each of said plurality of points of application on said front surface covers a surface area of from about 10 $\mu$m to about 100 $\mu$m in diameter.

5. The method of claim 2 wherein, each of said plurality of points of application on said front surface covers a surface area of from about 20 $\mu$m to about 50 $\mu$m in diameter.

6. The method of claim 2 wherein, said plurality of points of application of said acoustic wave to said front surface of said PEM are from about 0.1 mm to about 10 mm apart.

7. The method of claim 2 wherein, said plurality of points of application of said acoustic wave to said front surface of said PEM are from about 0.1 mm to about 1 mm apart.

8. The method of claim 2 wherein, said acoustic wave has a frequency of from about 5 MHz to about 2 GHz.

9. The method of claim 2 wherein, said acoustic wave has a frequency of from about 5 Mz to about 200 Mz.

10. The method of claim 1 wherein:
    applying said acoustic wave comprises using a coupling liquid which couple a source of said acoustic wave to said front surface of said PEM; and,
    detecting said acoustic wave comprises using a coupling liquid to couple a detector of said acoustic wave to said back surface of said PEM.

11. The method of claim 10 wherein said coupling liquid is maintained at a temperature of from about 1 degree above the freezing point of said coupling liquid to about 1 degree below the boiling point of said coupling liquid.

12. The method of claim 10 wherein, said coupling liquid is maintained at a temperature of from about 20° C. to about 60° C.

13. The method of claim 10 wherein said coupling liquid is maintained at a temperature of from about 22° C. to about 25° C.

14. The method of claim 10 wherein said coupling liquid is water.

15. The method of claim 1 wherein said acoustic wave is applied to said front surface of said PEM as a continuous acoustic wave.

16. The method of claim 1 wherein said acoustic wave is applied to said front surface of said PEM as an acoustic wave pulse.

17. A method for determining uniformity of the piezoelectric effect in a PEM comprising:
    applying an acoustic wave to a plurality of points on a front surface of said PEM;
    focusing said acoustic wave on a plurality of focal points on a back surface of said PEM, each of said plurality of focal points on said back surface corresponding to one of said points of application to said front surface of said PEM;

detecting at said front surface of said PEM an echo of said acoustic wave from each of said plurality of focal points on said back surface of said PEM;

determining a time-of-flight of said focussed acoustic wave at each of said plurality of focal points at said back surface; and, determining said uniformity of said piezoelectric effect by comparing each said time-of-flight at each of said plurality of focal points with said time-of-flight at each other of said plurality of focal points.

18. The method of claim 17 wherein:

said acoustic wave has a frequency of from 100 Hz to 8 GHz;

each of said plurality of points of application of said acoustic wave to said front surface covers a surface area of from about 5 $\mu$m to about 500 $\mu$m in diameter; and, said plurality of points of application of said acoustic wave to said front surface of said PEM are from about 0.1 mm to about 1 cm apart.

19. The method of claim 17 wherein determining said uniformity of said piezoelectric effect comprises using a cathode ray tube (CRT) display.

20. The method of claim 17 wherein each of said plurality of points of application of said acoustic wave to said front surface covers a surface area of from about 10 $\mu$m to about 100 $\mu$m in diameter.

21. The method of claim 17 wherein each of said plurality of points of application of said acoustic wave to said front surface covers a surface area of from about 20 $\mu$m to about 50 $\mu$m in diameter.

22. The method of claim 17 wherein said plurality of points of application of said acoustic wave to said front surface of said PEM are from about 0.1 mm to about 10 mm apart.

23. The method of claim 17 wherein said plurality of points of application of said acoustic wave to said front surface of said PEM are from about 0.1 mm to about 1.0 mm apart.

24. The method of claim 17 wherein, said acoustic wave has a frequency of from about 5 MHz to about 2 GHz.

25. The method of claim 17 wherein, said acoustic wave has a frequency of from about 5 Mz to about 200 Mz.

26. The method of claim 17 wherein said acoustic wave is applied as an acoustic wave pulse.

27. The method of claim 17 wherein:

applying said acoustic wave to said plurality of points on said front surface of said PEM comprises a coupling liquid to couple a source of said acoustic wave to said front surface of said PEM; and, detecting said echo of said acoustic wave from said plurality of focal points on said back surface comprises using a coupling liquid to couple a detector to said front surface of said PEM.

28. The method of claim 27 wherein said source of said acoustic wave is also using said detector of said acoustic wave.

29. The method of claim 27 wherein said coupling liquid is maintained at a temperature of from about 1 degree about the freezing point of said coupling liquid to about 1 degree below the boiling point of said coupling liquid.

30. The method of claim 27 wherein, said coupling liquid is maintained at a temperature of from about 20° C. to about 60° C.

31. The method of claim 27 wherein, said coupling liquid is maintained at a temperature of from about 22° C. to about 25° C.

32. The method of claim 27 wherein said coupling liquid is water.

33. A method for determining the piezoelectric effect created by poling a ferroelectric material (FEM) comprising:

applying an acoustic wave to a front surface of said FEM;

detecting said acoustic wave at a back surface of said FEM;

determining a first time-of-flight of said acoustic wave from said front surface of said FEM to said back surface of said FEM;

poling said FEM to create a PEM;

applying an acoustic wave to a said front surface of said PEM;

detecting said acoustic wave at said back surface of said PEM;

determining a second time-of-flight of said acoustic wave from said front surface of said PEM to said back surface of said PEM; and, determining said piezoelectric effect by comparing said first time-of-flight to said second time-of-flight.

34. A method for determining the piezoelectric effect created by poling a ferroelectric material (FEM) comprising:

applying an acoustic wave pulse to a plurality of points on a front surface of said FEM;

focusing said acoustic wave pulse on a plurality of focal points on a back surface of said FEM, each of said plurality of focal points on said back surface corresponding to one of said plurality of points of application to said front surface of said PEM;

detecting at said front surface of said FEM an echo of said acoustic wave pulse from each of said plurality of focal points on said back surface of said FEM;

determining a first time-of-flight of each of said acoustic wave pulses from each of said plurality of focal points on said back surface of said FEM;

poling said FEM material to create a PEM;

applying an acoustic wave pulse to a plurality of points on a front surface of said PEM;

focusing said acoustic wave pulse on a plurality of focal points on a back surface of said PEM, each of said focal points on said back surface corresponding to one of said plurality of points of application to said front surface of said PEM;

detecting at said front surface of said PEM an echo of said acoustic wave pulse from each of said plurality of focal points on said back surface of said PEM; and, determining a second time-of-flight of each said acoustic wave pulse from each said plurality of focal points on said back surface of said PEM; and, determining said piezoelectric effect by comparing each said first time-of-flight at each said plurality of focal points on said back surface of said FEM with each said second time-of-flight at each said plurality of focal points on said back surface of said PEM.

35. The method of any of claims 1, 17, 33 or 34 wherein, said method comprises using a scanning acoustic microscope (SAM).

* * * * *